(12) United States Patent
Lee et al.

(10) Patent No.: US 9,709,442 B2
(45) Date of Patent: Jul. 18, 2017

(54) SPECTRAL DETECTOR AND IMAGE SENSOR INCLUDING THE SAME

(71) Applicants: SAMSUNG ELECTRONICS CO., LTD., Suwon-si (KR); IMEC VZW, Leuven (BE)

(72) Inventors: Woochang Lee, Gwacheon-si (KR); Peter Peumans, Leuven (BE)

(73) Assignees: SAMSUNG ELECTRONICS CO., LTD., Suwon-si (KR); IMEC VZW, Leuven (BE)

( * ) Notice: Subject to any disclaimer, the term of this patent is extended or adjusted under 35 U.S.C. 154(b) by 0 days.

(21) Appl. No.: 15/297,720

(22) Filed: Oct. 19, 2016

(65) Prior Publication Data

US 2017/0167921 A1    Jun. 15, 2017

(30) Foreign Application Priority Data

Dec. 11, 2015 (KR) ........................ 10-2015-0177367

(51) Int. Cl.
| | | |
|---|---|---|
| *G01N 21/25* | (2006.01) | |
| *G01J 3/28* | (2006.01) | |
| *G01J 3/42* | (2006.01) | |
| *G01J 3/02* | (2006.01) | |
| *A61B 5/1455* | (2006.01) | |

(52) U.S. Cl.
CPC .......... *G01J 3/2823* (2013.01); *A61B 5/1455* (2013.01); *G01J 3/021* (2013.01); *G01J 3/42* (2013.01)

(58) Field of Classification Search
CPC ........ G01J 3/02; G01J 3/42; G01J 3/28; G01J 3/26; G01J 9/00; A61B 5/1455; G01N 21/255

See application file for complete search history.

(56) References Cited

U.S. PATENT DOCUMENTS

| | | | |
|---|---|---|---|
| 6,079,274 A | * | 6/2000 | Ando .................... G01H 11/08 310/321 |
| 6,643,421 B1 | | 11/2003 | Chin et al. |
| 7,796,262 B1 | | 9/2010 | Wang et al. |
| 8,611,747 B1 | | 12/2013 | Wach |
| 2012/0044489 A1 | | 2/2012 | Chakravarty et al. |

(Continued)

OTHER PUBLICATIONS

Arthur Nitkowski et al., "Cavity-enhanced on-chip absorption spectroscopy using microring resonators" Optics Express, vol. 16, No. 16, Aug. 4, 2008, 7 pages total.

(Continued)

*Primary Examiner* — Abdullahi Nur
(74) *Attorney, Agent, or Firm* — Sughrue Mion, PLLC (57) ABSTRACT

A spectral detector includes a plurality of spectral detection units, each of the spectral detection units including an optical signal processor configured to deliver an optical signal incident to the spectral detection unit to an outside of the spectral detection unit, and a resonator configured to modulate a spectrum of an optical signal incident to the optical signal processor by interacting with the optical signal processor, at least some of the resonators of the plurality of spectral detection units having different lengths from each other, and a number of optical signal processors included in each respective spectral detection unit varying according to a length of the resonator included in the respective spectral detection unit.

22 Claims, 8 Drawing Sheets (56) References Cited

U.S. PATENT DOCUMENTS

2013/0176554 A1   7/2013   Loncar et al.
2014/0085633 A1   3/2014   Preston et al.
2014/0233883 A1   8/2014   Sweeney et al.

OTHER PUBLICATIONS

Steve Zamek et al., "Micro-resonator with metallic mirrors coupled to a bus waveguide", Optics Express, vol. 19, No. 3, Jan. 31, 2011, 9 pages total.
Miroslaw Florjanczyk et al., "Multiaperture planar waveguide spectrometer formed by arrayed Mach-Zehnder interferometers", Optics Express, vol. 15, No. 26, Dec. 24, 2007, 14 pages total.

* cited by examiner

SPECTRAL DETECTOR AND IMAGE SENSOR INCLUDING THE SAME

CROSS-REFERENCE TO RELATED APPLICATION

This application claims priority from Korean Patent Application No. 10-2015-0177367, filed on Dec. 11, 2015, in the Korean Intellectual Property Office, the disclosure of which is incorporated herein in its entirety by reference.

BACKGROUND

1. Field

The exemplary embodiments disclosed herein relate to a spectral detector capable of analyzing a spectrum of incident light and an image sensor including the spectral detector.

2. Description of the Related Art

A method under current discussion as a noninvasive glucose measurement method is an analysis method based on a spectrum of light that is radiated to skin and then scattered from the skin, and includes a biometric signal. Recently, with improvement in performance of mobile devices such as cellular phones, various attempts have been made to integrate a noninvasive biometric sensor in a mobile device. To this end, a need exists for development of a micro spectral detector that is mountable in a mobile device.

For example, a spectral detector using a linear variable filter (LVF) scheme may have a structure in which a spacer having a gradually changing thickness is disposed on multiple photodiode pixels. By employing a principle that a transmissive wavelength changes with the thickness of the spacer, light in a different wavelength region may be sensed in a different pixel. A spectral detector using a filter array scheme has a structure in which a band-pass filter having a different transmissive band for a different photodiode pixel is disposed.

Recently, research has been conducted on a micro spectral detector based on silicon photonics. The silicon-photonics-based micro spectral detector may be manufactured to a small size in the form of a semiconductor chip, and thus is favorable to miniaturization.

SUMMARY

Exemplary embodiments disclosed herein may provide methods and apparatuses for detecting a spectrum of incident light.

Additional aspects will be set forth in part in the description which follows and, in part, will be apparent from the description, or may be learned by practice of the presented exemplary embodiments.

According to an aspect of an exemplary embodiment, there is provided a spectral detector including: a plurality of spectral detection units, each of the spectral detection units including: an optical signal processor configured to deliver an optical signal incident to the spectral detection unit to an outside of the spectral detection unit; and a resonator configured to modulate a spectrum of an optical signal incident to the optical signal processor by interacting with the optical signal processor, wherein at least some of the resonators of the plurality of spectral detection units have different lengths from each other, and a number of optical signal processors included in each respective spectral detection unit varies according to a length of the resonator included in the respective spectral detection unit.

In one of the spectral detection units, the resonator may be configured to absorb and resonate at least a part of the optical signal incident to the optical signal processor by interacting with the optical signal processor.

In one of the spectral detection units, the resonator may be configured to differently modulate a spectrum of the optical signal incident to the optical signal processor according to a length of the resonator.

In one of the spectral detection units, the optical signal processor may include: a light receiver configured to receive light incident thereon, the light including the optical signal; a waveguide configured to transmit the light incident to the light receiver; and an output unit configured to deliver the optical signal of the light that is modulated by the resonator while traveling through the waveguide to an outside of the spectral detection unit.

The waveguide may be configured to deliver at least a part of the light traveling therethrough to the resonator based on evanescent coupling.

The waveguide may include a bent portion that is provided adjacent to the resonator.

One of the plurality of spectral detection units may include a plurality of optical signal processors arranged in a lengthwise direction of the resonator of the one spectral detection unit.

The one spectral detection unit may include light receivers and output units of the plurality of optical signal processors that are arranged alternately with each other.

The one spectral detection unit may include light receivers of adjacent optical signal processors among the plurality of optical signal processors, the light receivers facing each other, and output units of adjacent optical signal processors among the plurality of optical signal processors, the output units facing each other.

In one of the spectral detection units, each of the light receiver and the output unit may include a plurality of mirrors arranged in a lattice structure.

According to an aspect of another exemplary embodiment, there is provided an image sensor including: a spectral detector including a plurality of spectral detection units; an optical measurer including a plurality of optical sensors corresponding to the plurality of spectral detection units, the plurality of optical sensors configured to measure optical signals output from the plurality of spectral detection units and to measure strength values of light based on the optical signals; and an image output unit configured to output an image of incident light based on the strength values of light which are measured by the plurality of optical sensors, wherein each of the plurality of spectral detection units includes: an optical signal processor configured to deliver an incident optical signal that is incident to the spectral detection unit to an outside of the spectral detection unit; and a resonator configured to modulate a spectrum of the incident optical signal that is incident to the optical signal processor by interacting with the optical signal processor; at least one of the optical signal processors is configured to output an electric signal as a strength of incident light including the incident optical signal; and a resonator configured to separate light having a predetermined wavelength from the incident light incident and to resonate the separated light, wherein at least some of the resonators of the plurality of spectral detection units have different lengths from each other, and a number of optical signal processors included in each respective spectral detection unit varies according to a length of the resonator included in the respective spectral detection unit.

In one of the spectral detection units, the resonator may be configured to absorb and resonate at least a part of the optical signal incident to the optical signal processor by interacting with the optical signal processor.

In one of the spectral detection units, the resonator may be configured to differently modulate a spectrum of the incident optical signal that is incident to the optical signal processor according to a length of the resonator.

A number of spectral detection units included in the spectral detector may vary according to lengths of the resonators.

The image sensor may further include: an optical signal adjuster configured to adjust the strength values of light which are measured by the plurality of optical sensors.

In one of the spectral detection units, the optical signal processor may include: a light receiver configured to receive light incident thereon, the light including the incident optical signal; a waveguide configured to transmit the light incident to the light receiver; and an output unit configured to deliver an optical signal of the light that is modulated by the resonator while traveling through the waveguide to an outside of the spectral detection unit.

The waveguide may be configured to deliver at least a part of the light traveling therethrough to the resonator based on evanescent coupling.

The waveguide may include a bent portion that is provided adjacent to the resonator.

One of the spectral detection units may include a plurality of optical signal processors arranged in a lengthwise direction of the resonator of the one spectral detection unit.

The one spectral detection unit may include light receivers and output units of the plurality of optical signal processors that are arranged alternately with each other.

The one spectral detection unit may include light receivers of adjacent optical signal processors among the plurality of optical signal processors, the light receivers facing each other, and output units of adjacent optical signal processors among the plurality of optical signal processors, the output units facing each other.

The image output unit may be configured to extract the image by analyzing a spectrum of the incident light based on the optical signals output from the plurality of spectral detection units.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the exemplary embodiments. Expressions such as "at least one of," when preceding a list of elements, modify the entire list of elements and do not modify the individual elements of the list.

Although terms used in exemplary embodiments are selected with general terms popularly used at present under the consideration of functions in the exemplary embodiments, the terms may vary according to the intention of those of ordinary skill in the art, judicial precedents, or introduction of new technology. In addition, in a specific case, the applicant voluntarily may select terms, and in this case, the meaning of the terms may be disclosed in a corresponding description of an aspect of the exemplary embodiments. Thus, the terms used in the exemplary embodiments should be defined not by the simple names of the terms but by the meaning of the terms and the description of the exemplary embodiments.

In a description of the exemplary embodiments, when a part is described as being connected to another part, the part may be not only directly connected to another part but may also be electrically connected to another part with yet another device intervening in between the parts. When a part is described as including an element, the part may also include another element(s), unless otherwise defined. The terms used in the exemplary embodiments, such as "unit" or "module", may indicate a unit for processing at least one function or operation, and may be implemented in hardware, software, or in a combination of hardware and software.

The terms such as "comprise" or "include" used in the exemplary embodiments should not be interpreted as necessarily including all of the elements or operations described herein, and may be interpreted as excluding some of the elements or operations or as further including additional elements or operations.

Although ordinal numbers such as "first" and "second" used in the various exemplary embodiments may modify various elements of the various exemplary embodiments, these terms do not limit the corresponding elements. These terms may be used for the purpose of distinguishing one element from another element.

The following description of the exemplary embodiments should not be construed as limiting the scope of the exemplary embodiments, and features which may be easily analogized or implemented by those of ordinary skill in the art should be construed as falling within the scope of the exemplary embodiments. Hereinafter, certain exemplary embodiments for illustrative purposes will be described in detail with reference to the accompanying drawings.

Figure 1:
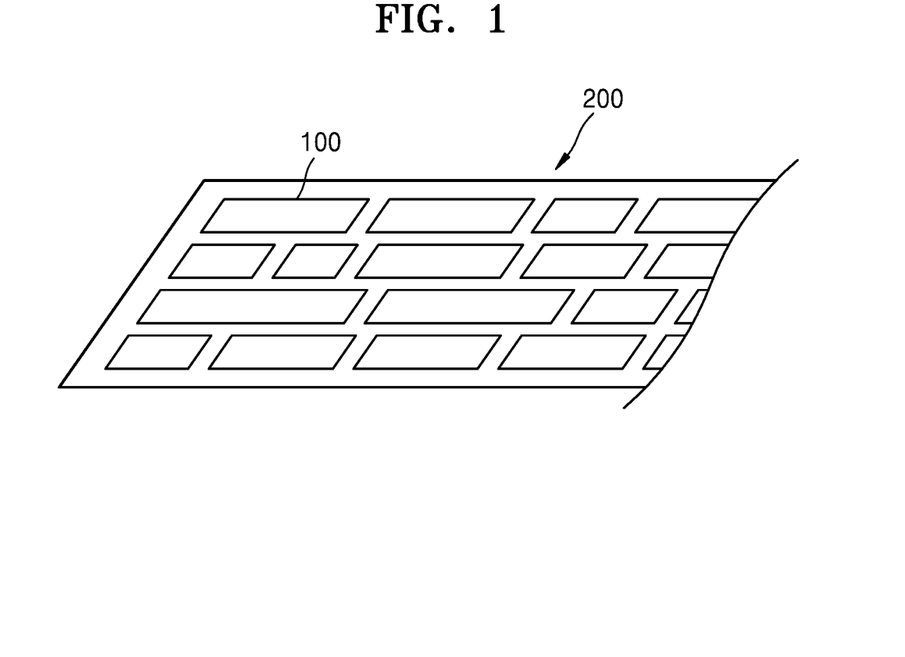
FIG. 1 is a perspective view of a spectral detector according to an exemplary embodiment.

FIG. 1 is a perspective view of a spectral detector 200 according to an exemplary embodiment.

Referring to FIG. 1, the spectral detector 200 may include a plurality of spectral detection units 100. The spectral detection units 100 of the spectral detector 200 may be formed by being patterned on a substrate such as an image sensor through rear-end processing based on silicon (Si) photonics. Once light is incident to the spectral detector 200, the spectral detection units 100 detect light in a wavelength region from the incident light. A size of each spectral detection unit 100 varies with the light's wavelength region detected by each spectral detection unit 100. As an example, the spectral detection units 100 included in the spectral detector 200 may have different sizes. As another example, a plurality of spectral detection units 100 having the same size may be included in the spectral detector 200.

Figure 2:
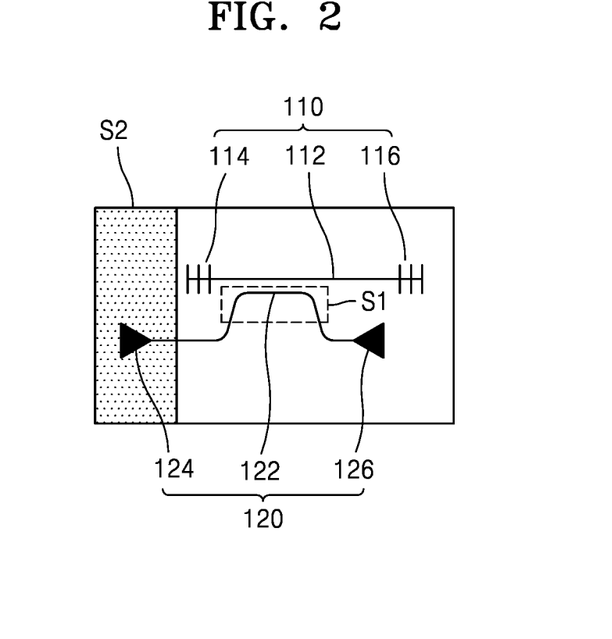
FIG. 2 illustrates an example of a spectral detection unit of a spectral detector illustrated in FIG. 1.

FIG. 2 illustrates an example of the spectral detection unit 100 of the spectral detector 200 illustrated in FIG. 1.

Referring to FIG. 2, each spectral detection unit 100 may include an optical signal processor 120 that delivers an optical signal incident to the spectral detection unit 100 to the outside of the spectral detection unit 100 and a resonator 110 that interacts with the optical signal processor 120 to modulate a spectrum (e.g., wavelength spectrum, frequency spectrum, etc.) of the optical signal incident to the optical signal processor 120.

The optical signal processor 120 may include a light receiver 124 to which light is incident, a waveguide 122 through which the light incident to the light receiver 124 travels, and an output unit 126 that delivers an optical signal of the light which is modulated by the resonator 110 while traveling through the waveguide 122 to the outside of the spectral detection unit 100. The light receiver 124 transmits, to the waveguide 122, the light incident to a region in the spectral detection unit 100 as an optical signal. The optical signal delivered by the light receiver 124 is delivered to the output unit 126 through the waveguide 122. The output unit 126 outputs the optical signal delivered through the waveguide 122 to the outside of the spectral detection unit 100. The output unit 126 may be arranged on a plane that is the same as or different from the waveguide 122 and the light receiver 124.

Figure 3:
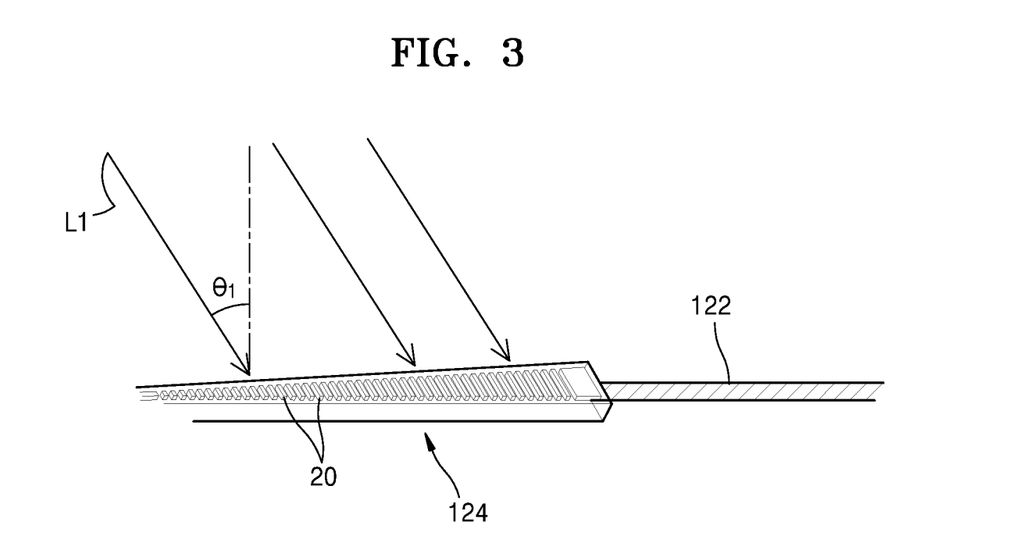
FIGS. 3 and 4 illustrate states where spectral detection units with the same width and different sizes are patterned.

FIG. 3 illustrates an example of the light receiver 124 illustrated in FIG. 2.

Referring to FIG. 3, the light receiver 124 delivers incident light L1 to the waveguide 122 by using a lattice structure in which materials having different refractive indices are repeatedly arranged. With mirrors 20 arranged under the lattice structure, the efficiency of delivery of the light L1 incident to the light receiver 124 may be improved. The mirrors 20 may be high-reflectance mirrors including metal. The incident light L1 may be incident at an incident angle of $\theta_1$ with respect to a plane where the light receiver 124 is positioned. For example, the incident angle $\theta_1$ may be about 15°. However, exemplary embodiments are not limited to this example, and the incident angle $\theta_1$ may vary according to an arrangement direction and an arrangement angle of the mirrors 20.

Figure 4:
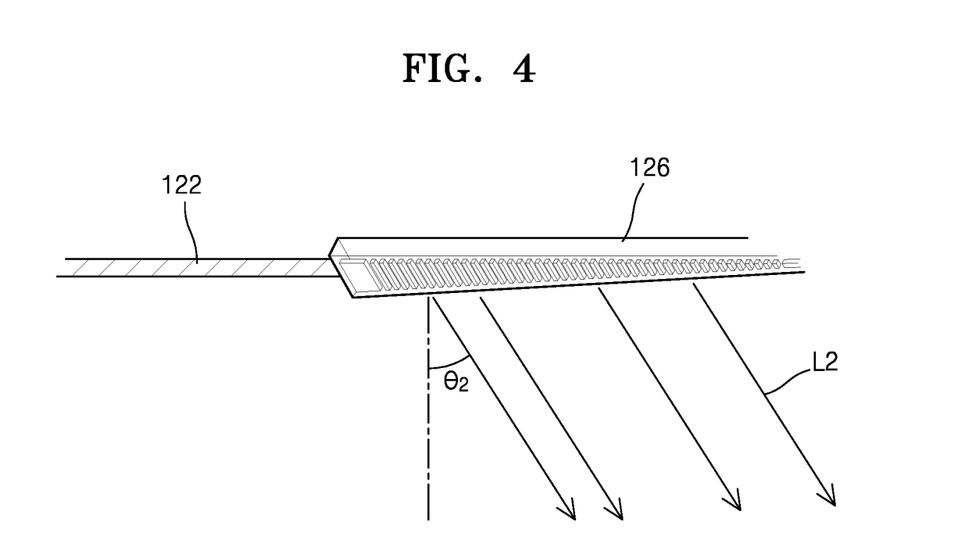

FIG. 4 illustrates an example of the output unit 126 illustrated in FIG. 2.

Referring to FIG. 4, the output unit 126 outputs, to the outside of the spectral detection unit 100, the light delivered through the waveguide 122 using the lattice structure in which the materials having the different refractive indices are repeatedly arranged. Light L2 output from the output unit 126 may be emitted at an emission angle of $\theta_2$ with respect to a plane where the output unit 126 is positioned. For example, the emission angle $\theta_2$ may be about 15°. However, exemplary embodiments are not limited to this example, and the emission angle $\theta_2$ may vary according to an arrangement and physical properties of the lattice structure.

The resonator 110 absorbs at least a part of the optical signal passing through the waveguide 122 of the optical signal processor 120. The resonator 110 may include the waveguide 112 and reflectors 114 and 116 provided on both ends of the waveguide 112. The reflectors 114 and 116 may be implemented with high-reflectance mirrors. To this end, the reflectors 114 and 116 may include a plurality of reflection plates.

The optical signal processor 120 delivers the optical signal to the resonator 110. To this end, the waveguide 122 of the optical signal processor 120 may include a bent portion S1 provided adjacent to the resonator 110. That is, the waveguide 122 may have a shape in which the portion S1 is bent to be close to the resonator 110. Once the optical signal is transmitted through the waveguide 122, evanescent coupling may occur between the waveguide 122 and the resonator 110 in the portion S1 adjacent to the resonator 110. Through evanescent coupling, the optical signal passing through the waveguide 122 of the optical signal processor 120 may be delivered to the waveguide 112 of the resonator 110.

By removing a wavelength component using evanescent coupling in the optical signal processor 120 in this way, optical signal processing efficiency may be enhanced when compared to a case with a Fabry-Perot resonator. Moreover, a signal-to-noise ratio (SNR) may also be improved.

Figure 5:
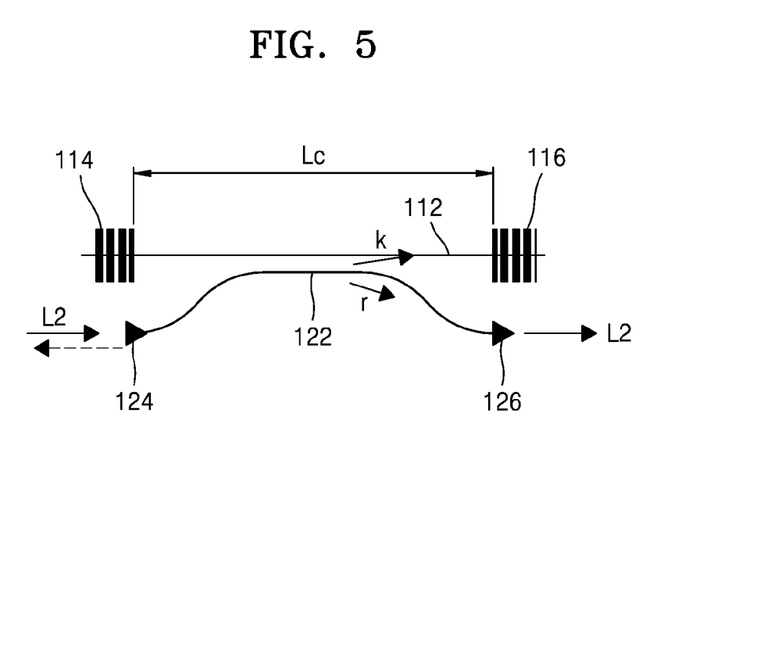
FIG. 5 is a view for describing an interaction between an optical signal processor and a resonator according to an exemplary embodiment.

FIG. 5 is a view for describing an interaction between the optical signal processor 120 and the resonator 110 according to an exemplary embodiment.

Referring to FIG. 5, through evanescent coupling, a part of an optical signal traveling through the waveguide 122 of the optical signal processor 120 may be delivered to the resonator 110. A coupling coefficient k indicates a rate of energy of light delivered to the resonator 110, out of the incident light L1. A transmission coefficient r indicates a rate of energy of the light L2 emitted from the output unit 126 by traveling through the waveguide 122 without being delivered to the resonator 110, out of the incident light L1. Thus, an equation, $r^2+k^2=1$, may be satisfied.

Once the optical signal is delivered to the resonator 110, the resonator 110 causes the delivered optical signal to travel therein. The resonator 110 may strongly resonate wavelength components near a resonant wavelength, out of the optical signal delivered from the waveguide 122. The resonant wavelength may be determined according to a length $L_C$ of the resonator 110. Then, the optical signal traveling through the waveguide 122 of the optical signal processor 120 may cause interference with the optical signal traveling in the resonator 110. The optical signal of the light L2 emitted from the output unit 126 after passing through the waveguide 122 and experiencing interference may be different from the optical signal of the incident light L1. That is, due to an interaction between the resonator 110 and the optical signal processor 120, a spectrum of the incident light L1 and a spectrum of the light L2 emitted from the output unit 126 may become different. This change in spectrum is because, due to interaction between the resonator 110 and the optical signal processor 120, a transmissivity of the incident light L1 with respect to the optical signal processor 120 changes according to a wavelength of the incident light L1.

For example, a transmissivity $T_{ec}$ at which the incident light L1 passes through the optical signal processor 120 according to a wavelength of the incident light L1 may be expressed according to Equation (1) as follows:

$$T_{ec} = \frac{r^2 a^2 - 2r^2 a\cos\left(n_{\textit{eff}}\frac{2\pi}{\lambda}L\right) + r^2}{1 - 2r^2 a\cos\left(n_{\textit{eff}}\frac{2\pi}{\lambda}L\right) + (r^2 a)^2} \quad \text{Equation (1)}$$

where L indicates two times of the length $L_C$ of the resonator 110 (that is, $L=2L_C$ is satisfied), $n_{\textit{eff}}$ indicates an effective refractive index of the waveguide 122 of the optical signal processor 120, and r indicates a rate of energy of the light L2 emitted from the output unit 126 by traveling through the waveguide 122 without being delivered to the resonator 110, out of the incident light L1. Also, the variable "a" may be expressed according to Equation (2) as follows:

$$a^2 = R^2 \exp(-\alpha L) \quad \text{Equation 2}$$

where R indicates a reflectance of the light receiver 124 and the output unit 126 of the optical signal processor 120, and a indicates an attenuation rate of the waveguide 122. For example, if the waveguide 122 includes silicon nitride, the attenuation rate of the waveguide 122 may be about 0.4 dB/cm. However, such material and such values are merely examples, and exemplary embodiments are not limited to these examples.

Referring to Equations 1 and 2, the transmissivity $T_{ec}$ of the incident light L1 passing through the optical signal processor 120 may vary according to a wavelength of the incident light L1. In Equation 1, $r^2$ may be obtained by measuring a strength of the light L2 emitted from the output unit 126 of the optical signal processor 120. L may be known from the length ($L_C=L/2$) of the resonator 110. By measuring the value $r^2$ while variously changing the length ($L_C=L/2$) of the resonator 110, the strength of a wavelength-specific component of the incident light L1 may be calculated from Equation 1. Since Equation 1 changes depending on the length ($L_C=L/2$) of the resonator 110, a greater number of equations may be obtained with a greater variance of distribution of the lengths ($L_C=L/2$) of the resonators 110 of the spectral detection units 100. In addition, as the number of times the strength of the light L2 output from the output unit 126 is measured while changing the length ($L_C=L/2$) of the resonator 110, strengths of more wavelength components may be calculated from the incident light L1.

The analysis of the spectrum of the incident light L1 becomes more accurate from Equation 1 as the length ($L_C=L/2$) of the resonator 110 is diversified, such that the spectral detector 200 may include the spectral detection units 100 having the resonators 110 with various lengths. At least some of the resonators 110 of the spectral detection units 100 included in the spectral detector 200 may have different lengths. For example, all the resonators 110 of the spectral detection units 100 may have different lengths. However, exemplary embodiments are not limited to this example. At least some of the resonators 110 may have different lengths, and some other resonators 110 may have the same length.

As the lengths of the resonators 110 of the spectral detection units 100 included in the spectral detector 200 according to an exemplary embodiment are diversified, the spectral detector 200 may detect an optical signal in various wavelength regions. Thus, as the size of the spectral detection units 100 included in the spectral detector 200 is diversified, a resolution of an optical signal detected by the spectral detector 200 may increase.

To implement a high-resolution spectral detector, information about various wavelength components of incident light has to be obtained. However, as can be seen from Equation 1, to obtain information about various wavelength components of incident light, the resonator 110 having a long length should be included in each spectral detection unit 100, causing an increase in the size of the spectral detection unit 100.

The increase in the size of the spectral detection unit 100 may limit the number of spectral detection units 100 that may be included in a limited space.

Figure 6:
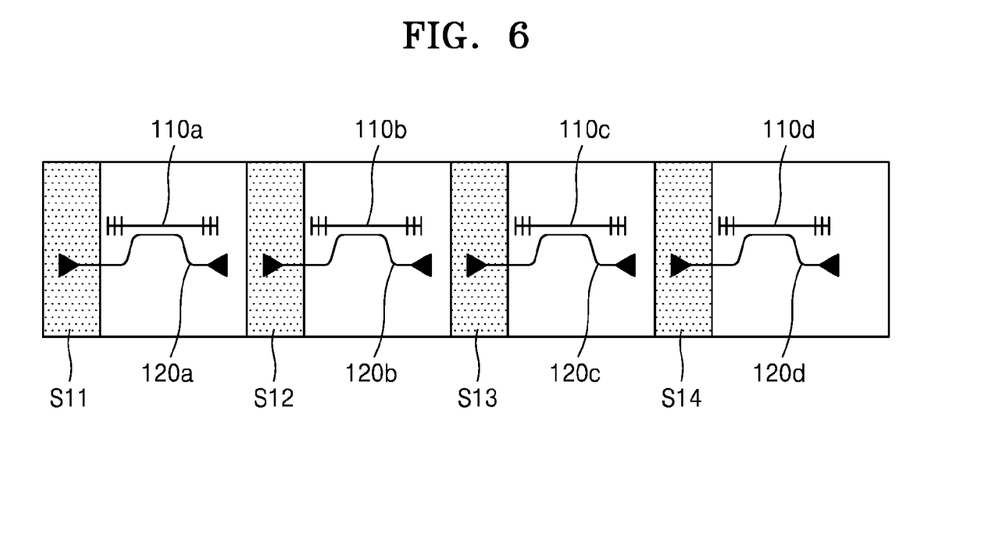
FIGS. 6 and 7 illustrate a state where spectral detection units having different sizes are patterned in the same area.
Figure 7:
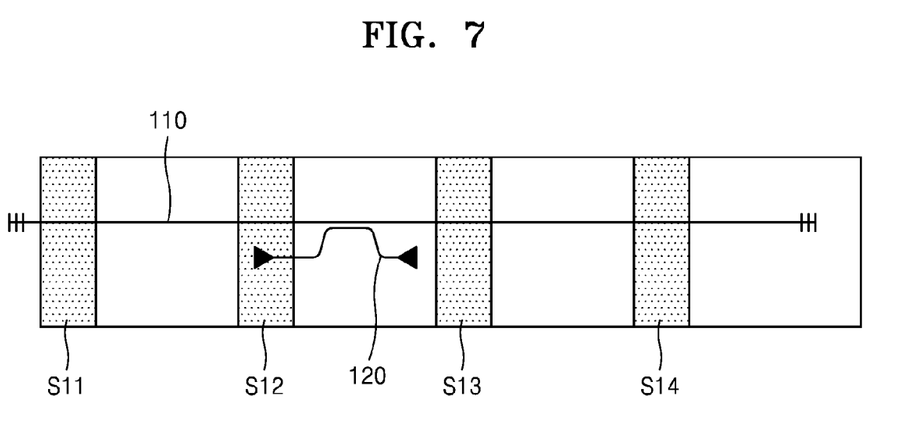

FIGS. 6 and 7 illustrate a state where the spectral detection units 100 having different sizes are patterned in the same area.

Referring to FIG. 6, four spectral detection units 100 may be provided in a line. On the other hand, referring to FIG. 7, in the same area as illustrated in FIG. 3, one spectral detection unit 100 may be provided. Since a length of the resonator 110 included in the spectral detection unit 100 illustrated in FIG. 7 is greater than lengths of first, second, third, and fourth resonators 110a, 110b, 110c, and 110d of the spectral detection units 100 illustrated in FIG. 6, the spectral detection unit 100 illustrated in FIG. 7 may occupy a larger area than the spectral detection units 100 illustrated in FIG. 6.

Referring to FIG. 6, first through fourth optical signal processors 120a, 120b, 120c, and 120d may be provided corresponding to the first through fourth resonators 110a, 110b, 110c, and 110d. The first optical signal processor 120a processes an optical signal incident to a first region S11. Likewise, the second through fourth optical signal processors 120b, 120c, and 120d may process optical signals incident to second through fourth regions S12, S13, and S14, respectively.

On the other hand, referring to FIG. 7, in the same area as illustrated in FIG. 6, one resonator 110 may be provided. The resonator 110 illustrated in FIG. 7 may resonate light having higher wavelengths than those of the first through fourth resonators 110a, 110b, 110c, and 110d illustrated in FIG. 6. Thus, the spectral detection unit 100 illustrated in FIG. 7 may detect an optical signal of light obtained by removing high-wavelength components from incident light when compared to the spectral detection units 100 illustrated in FIG. 6.

If the resonator 110 and the optical signal processor 120 correspond to each other in a one-to-one configuration as shown in FIG. 7, optical signal processing efficiency may be degraded for the long-length resonator 110. For example, as illustrated in FIG. 7, if the optical signal processor 120 is arranged corresponding to the resonator 110, the optical signal processor 120 processes an optical signal of light incident to the second region S12. In this case, optical signals of light incident to the first region S11, the third region S13, and the fourth region S14 may not be processed. As a result, when compared to FIG. 6, an optical throughput per unit area may be lowered. That is, space use efficiency may be deteriorated in the spectral detection unit 100 including the long-length resonator 110.

According to an exemplary embodiment, to maintain an optical throughput per unit area at a specific level or higher regardless of the length of the resonator 110 included in the spectral detection unit 100, the number of optical signal processors 120 may vary from one spectral detection unit 100 to another spectral detection unit 100. For example, the number of optical signal processors 120 included in each spectral detection unit 100 may vary with a length of the resonator 110 included in each spectral detection unit 100.

Figure 8:
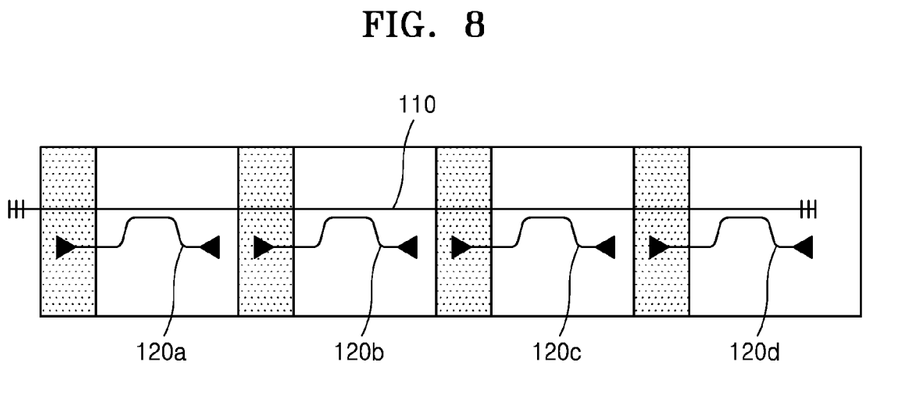
FIG. 8 illustrates an example of a spectral detection unit included in a spectral detector according to an exemplary embodiment.

FIG. 8 illustrates an example of the spectral detection unit 100 included in the spectral detector 200 according to an exemplary embodiment.

Referring to FIG. 8, a plurality of optical signal processors 120a, 120b, 120c, and 120d are included in one spectral detection unit 100. For example, the optical signal processors 120a, 120b, 120c, and 120d may be arranged in a lengthwise direction of the resonator 110.

In FIG. 8, the optical signal processors 120a, 120b, 120c, and 120d are arranged in a line below the resonator 110. However, exemplary embodiments are not limited to this example. In another example, the optical signal processors 120a, 120b, 120c, and 120d may be arranged both above and below the resonator 110. The number of optical signal processors 120 included in each spectral detection unit 100 may vary. For example, as the length of the resonator 110 included in the spectral detection unit 100 increases, the number of optical signal processors 120 included in the spectral detection unit 100 may increase.

The plurality of optical signal processors 120a, 120b, 120c, and 120d process a signal of light incident to different regions. Waveguides of the plurality of optical signal processors 120a, 120b, 120c, and 120d may include a portion adjacent to the corresponding resonators 110. Each of the optical signal processors 120a, 120b, 120c, and 120d delivers at least a part of an optical signal to the resonator 110 through evanescent coupling. The resonator 110 resonates a resonant wavelength component corresponding to the length of the resonator 110. Through the resonator 110, each of the optical signal processors 120a, 120b, 120c, and 120d detects an optical signal in which a resonant wavelength component is removed.

If the plurality of optical signal processors 120a, 120b, 120c, and 120d are provided for one resonator 110 as illustrated in FIG. 8, an optical throughput per unit area in the spectral detection unit 110 may increase. As the optical throughput per unit area in the spectral detection unit 110 increases, the strength of the optical signal output from the spectral detection unit 100 may increase. In this way, an SNR of the optical signal measured in the spectral detection unit 100 may increase.

The optical signal processors 120a, 120b, 120c, and 120d illustrated in FIG. 8 may be arranged in the lengthwise direction of the resonator 110. However, exemplary embodiments are not limited thereto, and the optical signal processors 120a, 120b, 120c, and 120d may be arranged in various other ways as well.

Figure 9:
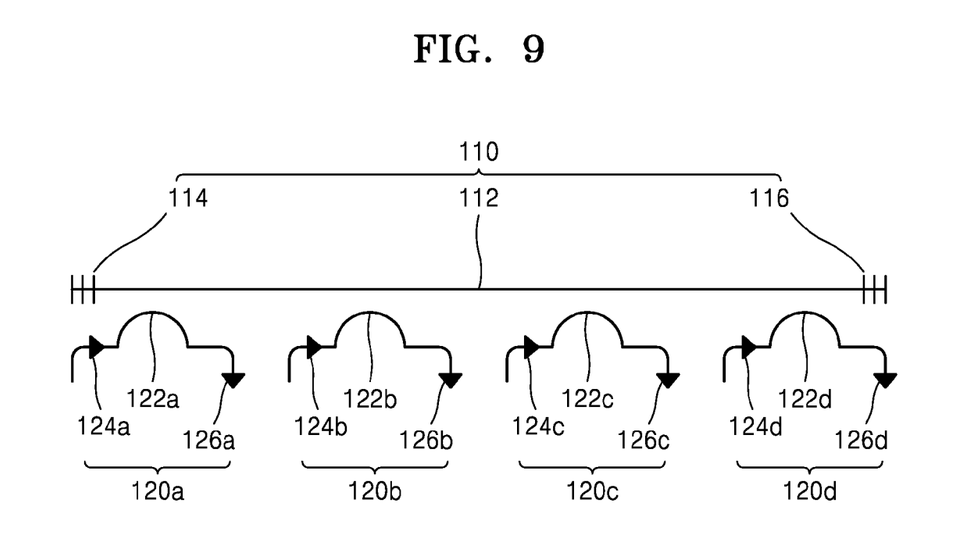
FIGS. 9 and 10 illustrate an arrangement of optical signal processors illustrated in FIG. 8 according to exemplary embodiments.
Figure 10:
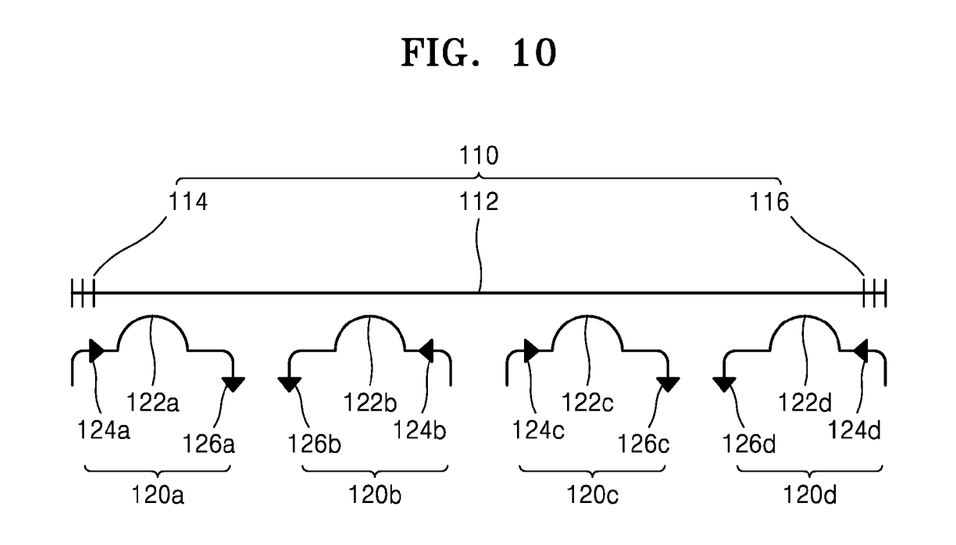

FIGS. 9 and 10 illustrate an arrangement of the optical signal processors 120a, 120b, 120c, and 120d illustrated in FIG. 8 according to exemplary embodiments. In FIGS. 9 and 10, arrows indicate directions in which an optical signal is transmitted.

Referring to FIG. 9, first, second, third, and fourth light receivers 124a, 124b, 124c, and 124d and first, second, third, and fourth output units 126a, 126b, 126c, and 126d of the optical signal processors 120a, 120b, 120c, and 120d may be arranged alternately. Also, in the optical signal processors 120a, 120b, 120c, and 120d, the light receivers 124a, 124b, 124c, and 124d and the output units 126a, 126b, 126c, and 126d may be arranged in the same direction. In this case, in the optical signal processors 120a, 120b, 120c, and 120d, an optical signal may be transmitted in the same direction.

Referring to FIG. 10, light receivers of adjacent optical signal processors out of the optical signal processors 120a, 120b, 120c, and 120d may be arranged to face each other. For example, the second light receiver 124b of the second optical signal processor 120b and the third light receiver 124c of the third optical signal processor 120c may face each other. Output units of adjacent optical signal processors may also be arranged to face each other. For example, the first output unit 126a of the first optical signal processor 120a and the second output unit 126b of the second optical signal processor 120b may face each other. The third output unit 126c of the third optical signal processor 120c and the fourth output unit 126d of the fourth optical signal processor 120d may also face each other.

If the plurality of optical signal processors 120a, 120b, 120c, and 120d are arranged as illustrated in FIG. 10, light receivers and output units of adjacent optical signal processors may be arranged in opposite directions. Thus, optical signal processing directions of the optical signal processors 120a, 120b, 120c, and 120d arranged in the lengthwise direction of the resonator 110 may change in an alternating fashion.

The exemplary embodiments illustrated in FIGS. 9 and 10 are merely examples, and an arrangement of the optical signal processors 120a, 120b, 120c, and 120d may be changed in various ways. For example, arrangement directions of the light receivers 124a, 124b, 124c, and 124d and the output units 126a, 126b, 126c, and 126d of the optical signal processors 120a, 120b, 120c, and 120d may be changed irregularly.

Figure 11:
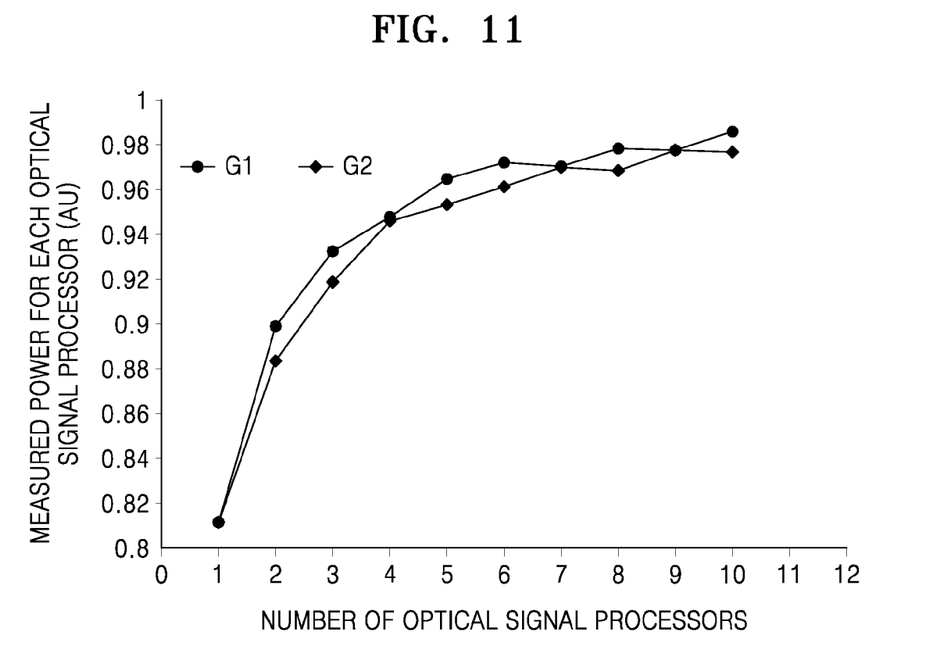
FIG. 11 is a graph showing a change in a strength of an optical signal measured for each optical signal processor in relation to a changing number of optical signal processors according to the exemplary embodiments illustrated in FIGS. 9 and 10.

FIG. 11 is a graph showing a change in a strength of an optical signal measured for each optical signal processor 120 in relation to a changing number of optical signal processors 120 according to the exemplary embodiments illustrated in FIGS. 9 and 10. Herein, a strength of an optical signal measured for the optical signal processor 120 indicates a strength of an electric signal into which the output unit 126 of the optical signal processor 120 converts the optical signal.

In FIG. 11, a horizontal axis plots the number of optical signal processors 120 included in the spectral detection unit 100 and a vertical axis plots a strength of an optical signal measured for each optical signal processor 120. The vertical axis plots a dimensionless number indicating a magnitude of a strength of an optical signal output for each optical signal processor 120 when an intensity of light input for each optical signal processor 120 is set to 1.

A graph G1 shows experimental results when the optical signal processors 120 are arranged according to the arrangement illustrated in FIG. 9. A graph G2 shows experimental results when the optical signal processors 120 are arranged according to the arrangement illustrated in FIG. 10.

Referring to FIG. 11, as the number of optical signal processors 120 increases, the strength of the optical signal measured for each optical signal processor 120 increases, regardless of an arrangement of the optical signal processors 120. The strength of the optical signal measured for each optical signal processor 120 is proportional to a square root of the number of optical signal processors 120. That is, when the number of optical signal processors 120 is N, the strength of the optical signal measured for each optical signal processor 120 is $\sqrt{N}$ times as large as the strength of the optical signal measured for each optical signal processor 120 when the number of optical signal processors 120 is 1. This feature is because there may be optical signal reinforcement between the optical signal processors 120.

Thus, by providing the plurality of optical signal processors 120 in the spectral detection unit 100 according to exemplary embodiments, an optical throughput for each optical signal processor 120 may increase.

Figure 12:
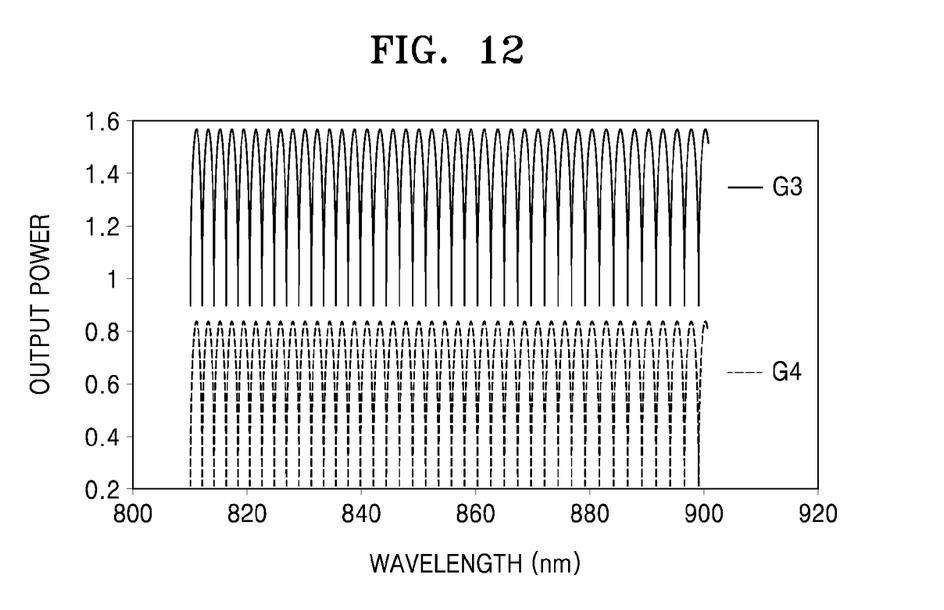
FIG. 12 is a graph showing a change in an optical signal output power of a spectral detection unit with respect to the number of optical signal processors included in a spectral detection unit.

FIG. 12 is a graph showing a change in an optical signal output power of the spectral detection unit 100 with respect to the number of optical signal processors 120 included in the spectral detection unit 100. Herein, the optical signal output power refers to a power indicated by a sum of electric signals output from the output units 126 of the optical signal processors 120 of the spectral detection unit 100.

In FIG. 12, a horizontal axis plots a wavelength of an optical signal and a vertical axis plots a dimensionless number indicating a magnitude of a strength of an optical signal output for each optical signal processor 120 when an intensity of light input for each optical signal processor 120 is set to 1.

A graph G4 indicates a case where one optical signal output unit 120 is included in the spectral detection unit 100, and a graph G3 indicates a case where two optical signal output units 120 are included in the spectral detection unit 100.

Referring to FIG. 12, it can be seen that the graph G3 has a globally higher signal strength level than the graph G4 while maintaining the same shape as the graph G3. That is, regardless of the number of optical signal output units 120, the shape of a spectrum of an optical signal may be maintained. Furthermore, as the number of optical signal output units 120 increases, an output power level of an optical signal measured in the spectral detection unit 100 may be increased. In this way, an SNR may be increased, and an optical signal at a high level may be obtained even when a strength of light incident to the spectral detection unit 100 is small.

Figure 13:
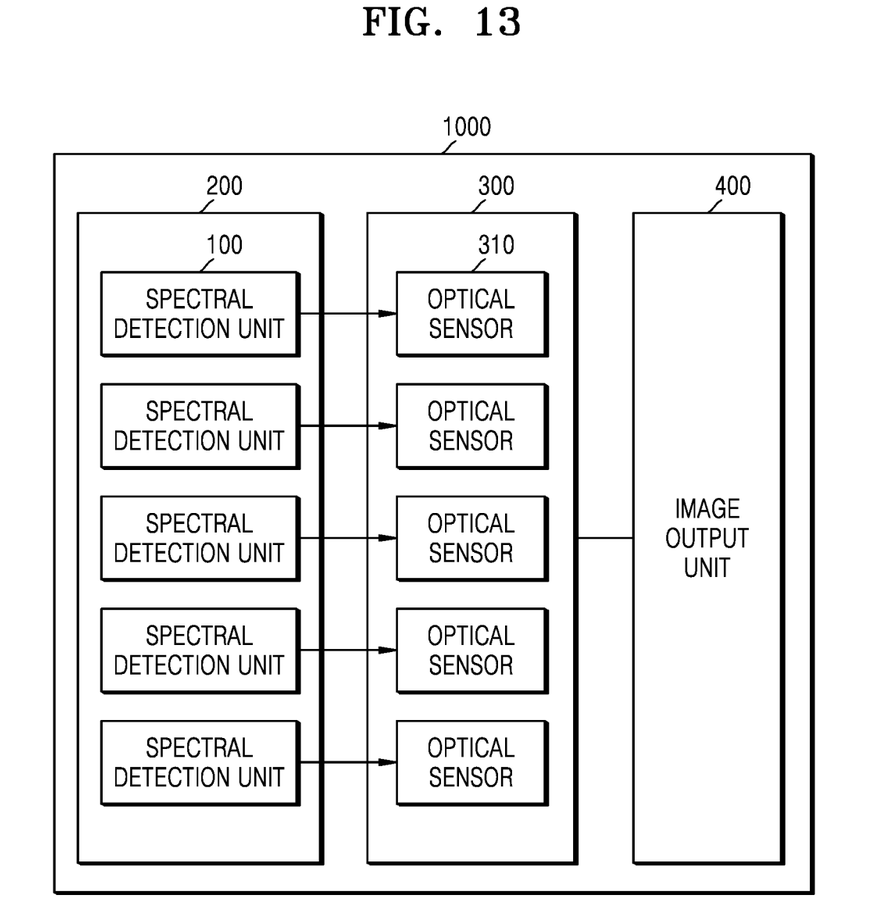
FIG. 13 is a block diagram of an image sensor including a spectral detector according to an exemplary embodiment.

FIG. 13 is a block diagram of an image sensor 1000 including the spectral detector 200 according to an exemplary embodiment.

Referring to FIG. 13, the image sensor 1000 may include the spectral detector 200 including the plurality of spectral detection units 100, an optical measurer 300 including a plurality of optical sensors 310, each of which is provided for a corresponding spectral detection unit 100 and measures an optical signal output from the corresponding spectral detection unit 100, and an image output unit 400 that outputs an image of incident light from strength values of the light measured by the optical measurer 300.

The spectral detector 200, the optical measurer 300, and the image output unit 400 may be provided for each pixel of the image sensor 1000. The spectral detector 200, the optical measurer 300, and the image output unit 400 may be provided for a plurality of pixels of the image sensor 1000. Thus, in the image sensor 1000, a plurality of spectral detectors 200, a plurality of optical measurers 300, and a plurality of output units 400 may be provided. The exemplary embodiments described above with reference to FIGS. 1 through 12 may be applied to the spectral detector 200 illustrated in FIG. 13.

With an increase in a variety of types of the resonator 110 included in the spectral detection unit 100 of the spectral detector 200, higher-resolution spectral detection may be performed. The spectral detection units 100 may include the resonators 110 having different lengths.

The number of spectral detection units 100 included in the spectral detector 200 may change according to the length of the resonator 110 included in the spectral detection unit 100. For example, in the spectral detection unit 100 including the long-length resonator 110, a relatively large number of optical signal output units 120 may be included, thus detecting an optical signal at a high level. On the other hand, the spectral detection unit 100 including the short-length resonator 110 has a small light-receiving area, thus detecting an optical signal at a low level. As a result, the number of spectral detection units 100 including the short-length resonators 110 may be greater than the number of spectral detection units 100 including the long-length resonators 100.

The optical sensors 310 of the optical measurer 300 measure optical signals output from the spectral detection units 100. Light output from the output unit 126 of the optical signal processor 120 in the spectral detection unit 100 is incident to the optical sensor 310.

The image output unit 400 analyzes a spectrum of the light incident to the spectral detector 200 from the optical signal measured by the optical sensor 310. The spectral detection units 100 include the resonators 110 having different lengths, such that the spectral detection units 100 differently modulate a spectrum of the incident light L1 and deliver the incident light L1 to the optical sensors 310 of the optical measurer 300. The image output unit 400 calculates the spectrum of the light incident to the spectral detection units 100 from the strength values of the light measured by the optical sensors 310 by using Equation 1.

By using the spectrum of the incident light, the image output unit 400 generates the image of the light incident to the spectral detector 200.

However, as the number of optical signal processors 120 changes according to the length of the resonator 110 included in the spectral detection unit 100, an optical signal output level may also vary from the spectral detection unit 100 to the spectral detection unit 100. When the optical signal output level changes with the spectral detection unit 100, an error may occur when the image output unit 400 analyzes the spectrum of the incident light. For example, if the optical signal output level of the spectral detection unit 100 varies with the length of the resonator 110, an optical signal output level may also change with a wavelength region, such that a relative strength for each wavelength of the incident light may not be properly analyzed when the spectrum of the incident light is analyzed.

Figure 14:
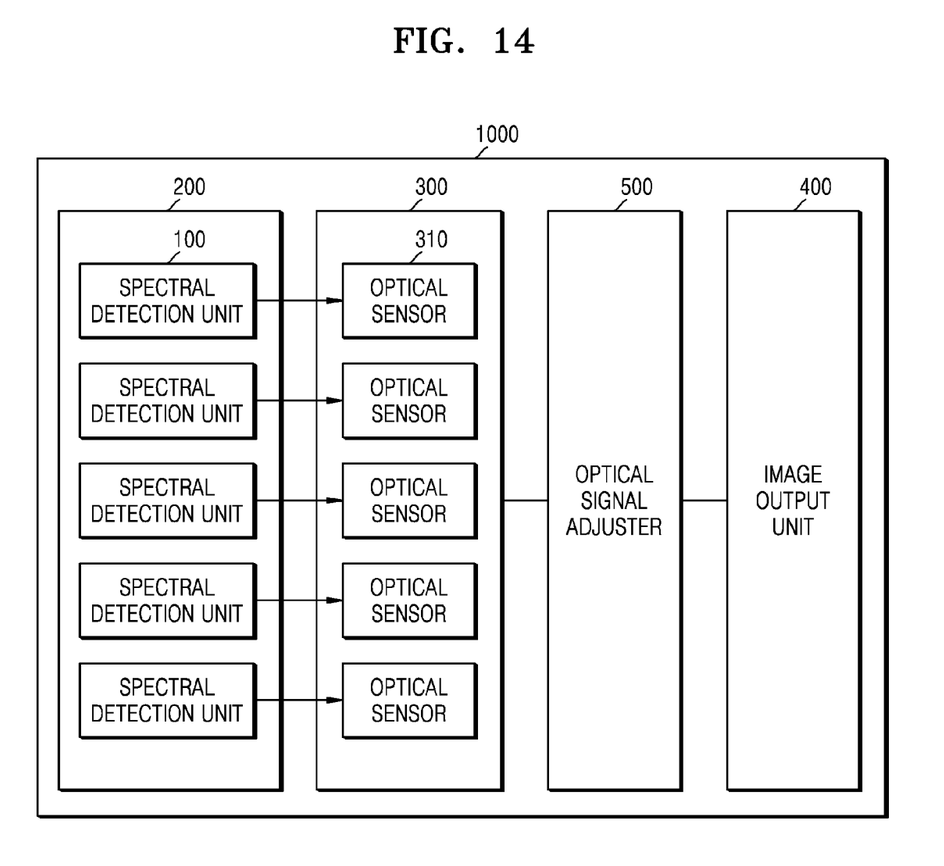
FIG. 14 is a block diagram of an image sensor according to an exemplary embodiment.

FIG. 14 is a block diagram of the image sensor 1000 according to an exemplary embodiment.

Referring to FIG. 14, the image sensor 1000 may further include an optical signal adjuster 500 that adjusts a strength of an electric signal output from the optical signal processor 120 of the spectral detection unit 100. As the number of optical signal processors 120 included in the spectral detection unit 100 increases, a level of an optical signal output from each spectral detection unit 100 may increase. In this context, the optical signal adjuster 500 receives a strength value of an optical signal measured by each optical sensor 310 and adjusts the received strength value of the optical signal. In this case, the optical signal adjuster 500 may adjust measurement values of optical signals measured by the optical sensors 310, taking the number of optical signal processors 120 included in the spectral detection unit 100 and the number of spectral detection units 100 including the resonators 110 having the same length into account. Once the optical signal adjuster 300 delivers the adjusted measurement values to the image output unit 400, the image output unit 400 analyzes the spectrum of the incident light based on the delivered adjusted measurement values.

With reference to FIGS. 1 through 14, a description will be made of the spectral detector 200 and the image sensor 1000 including the spectral detector 200. As described above, the spectral detector 200 may be configured to perform evanescent coupling. Moreover, by changing the number of optical signal output units 120 according to the length of the resonator 110 of the spectral detector 200, the space use efficiency of the spectral detector 200 may be improved and an SNR may also be improved.

While various details have been described above, the details should be interpreted as providing examples of exemplary embodiments rather than limiting the scope of the exemplary embodiments. Therefore, the scope of the exemplary embodiments should be defined by the technical spirit of the claims rather than by the described exemplary embodiments.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the exemplary embodiments as defined by the following claims.

What is claimed is:

1. A spectral detector comprising:
a plurality of spectral detection units, each of the spectral detection units comprising:
an optical signal processor configured to deliver an optical signal incident to the spectral detection unit to an outside of the spectral detection unit; and
a resonator configured to modulate a spectrum of an optical signal incident to the optical signal processor by interacting with the optical signal processor,
wherein at least some of the resonators of the plurality of spectral detection units have different lengths from each other, and a number of optical signal processors included in each respective spectral detection unit varies according to a length of the resonator included in the respective spectral detection unit.

2. The spectral detector of claim 1, wherein, in one of the spectral detection units, the resonator is configured to absorb and resonate at least a part of the optical signal incident to the optical signal processor by interacting with the optical signal processor.

3. The spectral detector of claim 1, wherein, in one of the spectral detection units, the resonator is configured to differently modulate a spectrum of the optical signal incident to the optical signal processor according to a length of the resonator.

4. The spectral detector of claim 1, wherein, in one of the spectral detection units, the optical signal processor comprises:
a light receiver configured to receive light incident thereon, the light comprising the optical signal;
a waveguide configured to transmit the light incident to the light receiver; and
an output unit configured to deliver the optical signal of the light that is modulated by the resonator while traveling through the waveguide to an outside of the spectral detection unit.

5. The spectral detector of claim 4, wherein the waveguide is configured to deliver at least a part of the light traveling therethrough to the resonator based on evanescent coupling.

6. The spectral detector of claim 5, wherein the waveguide comprises a bent portion that is provided adjacent to the resonator.

7. The spectral detector of claim 4, wherein one of the plurality of spectral detection units comprises a plurality of optical signal processors arranged in a lengthwise direction of the resonator of the one spectral detection unit.

8. The spectral detector of claim 7, wherein the one spectral detection unit comprises light receivers and output units of the plurality of optical signal processors that are arranged alternately with each other.

9. The spectral detector of claim 7, wherein the one spectral detection unit comprises light receivers of adjacent optical signal processors among the plurality of optical signal processors, the light receivers facing each other, and output units of adjacent optical signal processors among the plurality of optical signal processors, the output units facing each other.

10. The spectral detector of claim 4, wherein, in one of the spectral detection units, each of the light receiver and the output unit comprises a plurality of mirrors arranged in a lattice structure.

11. An image sensor comprising:
a spectral detector comprising a plurality of spectral detection units;
an optical measurer comprising a plurality of optical sensors corresponding to the plurality of spectral detection units, the plurality of optical sensors configured to measure optical signals output from the plurality of spectral detection units and to measure strength values of light based on the optical signals; and
an image output unit configured to output an image of incident light based on the strength values of light which are measured by the plurality of optical sensors,
wherein each of the plurality of spectral detection units comprises:
an optical signal processor configured to deliver an incident optical signal that is incident to the spectral detection unit to an outside of the spectral detection unit; and
a resonator configured to modulate a spectrum of the incident optical signal that is incident to the optical signal processor by interacting with the optical signal processor;
at least one of the optical signal processors is configured to output an electric signal as a strength of incident light comprising the incident optical signal; and
a resonator configured to separate light having a predetermined wavelength from the incident light incident and to resonate the separated light,
wherein at least some of the resonators of the plurality of spectral detection units have different lengths from each other, and a number of optical signal processors included in each respective spectral detection unit varies according to a length of the resonator included in the respective spectral detection unit.

12. The image sensor of claim 11, wherein, in one of the spectral detection units, the resonator is configured to absorb and resonate at least a part of the optical signal incident to the optical signal processor by interacting with the optical signal processor.

13. The image sensor of claim 11, wherein, in one of the spectral detection units, the resonator is configured to differently modulate a spectrum of the incident optical signal that is incident to the optical signal processor according to a length of the resonator.

14. The image sensor of claim 11, wherein a number of spectral detection units included in the spectral detector varies according to lengths of the resonators.

15. The image sensor of claim 11, further comprising:
an optical signal adjuster configured to adjust the strength values of light which are measured by the plurality of optical sensors.

16. The image sensor of claim 11, wherein, in one of the spectral detection units, the optical signal processor comprises:
a light receiver configured to receive light incident thereon, the light comprising the incident optical signal;
a waveguide configured to transmit the light incident to the light receiver; and
an output unit configured to deliver an optical signal of the light that is modulated by the resonator while traveling through the waveguide to an outside of the spectral detection unit.

17. The image sensor of claim 16, wherein the waveguide is configured to deliver at least a part of the light traveling therethrough to the resonator based on evanescent coupling.

18. The image sensor of claim 17, wherein the waveguide comprises a bent portion that is provided adjacent to the resonator.

19. The image sensor of claim 16, wherein one of the spectral detection units comprises a plurality of optical signal processors arranged in a lengthwise direction of the resonator of the one spectral detection unit.

20. The image sensor of claim 19, wherein the one spectral detection unit comprises light receivers and output units of the plurality of optical signal processors that are arranged alternately with each other.

21. The image sensor of claim 19, wherein the one spectral detection unit comprises light receivers of adjacent optical signal processors among the plurality of optical signal processors, the light receivers facing each other, and output units of adjacent optical signal processors among the plurality of optical signal processors, the output units facing each other.

22. The image sensor of claim 11, wherein the image output unit is configured to extract the image by analyzing a spectrum of the incident light based on the optical signals output from the plurality of spectral detection units.

* * * * *